United States Patent [19]

Nafissi-Varchei

[11] Patent Number: 4,512,998
[45] Date of Patent: Apr. 23, 1985

[54] ANTHELMINTIC BENZIMIDAZOLE CARBAMATES

[75] Inventor: M.Mehdi Nafissi-Varchei, North Caldwell, N.J.

[73] Assignee: Schering Corporation, Kenilworth, N.J.

[21] Appl. No.: 198,423

[22] Filed: Oct. 20, 1980

[51] Int. Cl.³ ............... A61K 31/425; A61K 31/415; C07D 417/02; C07D 513/04
[52] U.S. Cl. .................... 514/367; 548/154; 548/159; 548/181; 548/186; 548/189; 548/194; 548/306; 548/329; 548/337; 514/365; 514/368; 514/395
[58] Field of Search ............... 548/154, 159, 181, 306; 424/270, 273 B

[56] References Cited

U.S. PATENT DOCUMENTS 3,901,901  8/1975  Beard ........................ 548/154
3,935,209  1/1976  Beard et al. ............... 548/306 X
3,969,526  7/1976  Gyurik et al. ............. 548/306 X Primary Examiner—Richard A. Schwartz
Attorney, Agent, or Firm—Anita W. Magatti; Stephen I. Miller

[57] ABSTRACT

Compounds of the formula

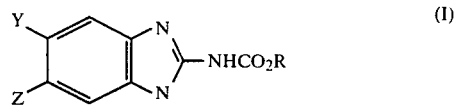

wherein R is alkyl having 1 to 4 carbon atoms, one of Y and Z is a heterocyclic moiety, and the other of Y and Z is hydrogen, alkyl having 1 to 4 carbon atoms or alkoxy having 1 to 4 carbon atoms are useful as anthelmintics.

8 Claims, No Drawings

ANTHELMINTIC BENZIMIDAZOLE CARBAMATES

The present invention relates to novel benzimidazole carbamates.

The compounds of the present invention are compounds of the formula

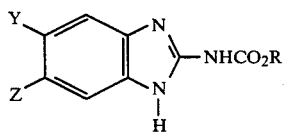

wherein R is alkyl having 1 to 4 carbon atoms, one of Y and Z is a heterocyclic moiety, and the other of Y and Z is hydrogen, alkyl having 1 to 4 carbon atoms or alkoxy having 1 to 4 carbon atoms.

The heterocyclic moiety is selected from

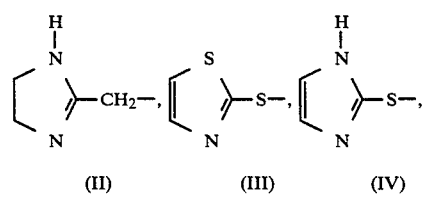

(II)   (III)   (IV)

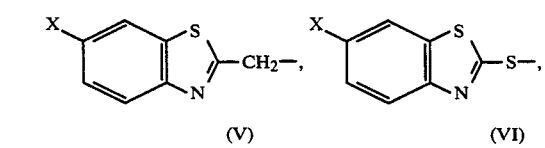

(V)   (VI)

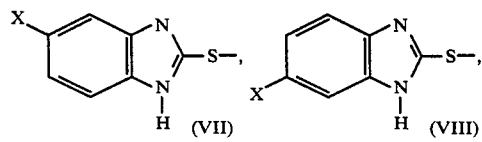

(VII)   (VIII)

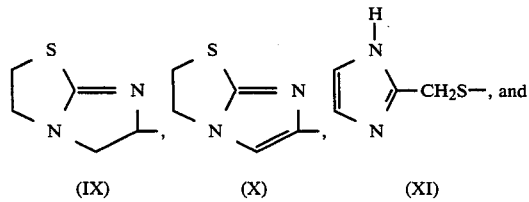

(IX)   (X)   (XI)

(XII)

The present invention also relates to methods of preparing the aforementioned compounds and to the use of said compounds as anthelmintics.

The following reaction scheme illustrates the preparation of compounds of the formula I wherein one of Y and Z is selected from groups of the formula III, IV, VI, VII, VIII, XI and XII;

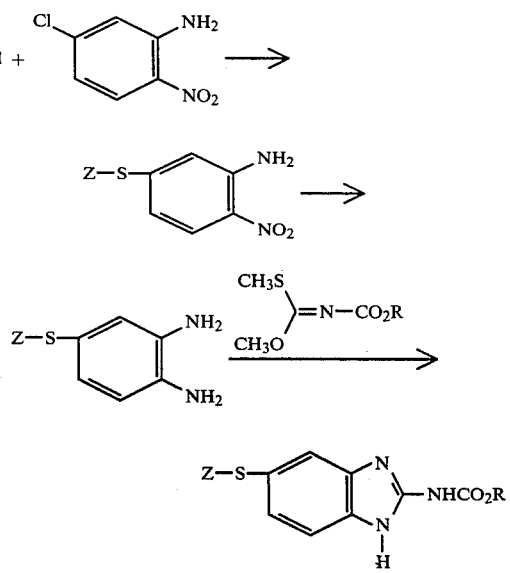

The method shown above is further exemplified by Preparation A and Example 1 below.

The following reaction scheme illustrates the preparation of compounds of the formula I wherein Z or Y is IX or X.

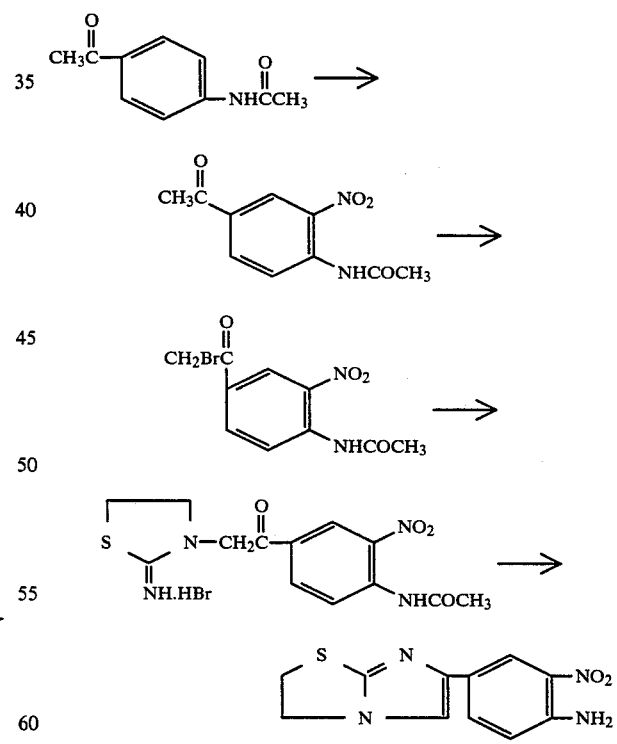

The above intermediate is then further reacted as shown in the previous reaction scheme. This method is further exemplified in Example 2.

The following reaction scheme illustrates the preparation of compounds of the formula I wherein one of Y and Z is a group of the formula II:

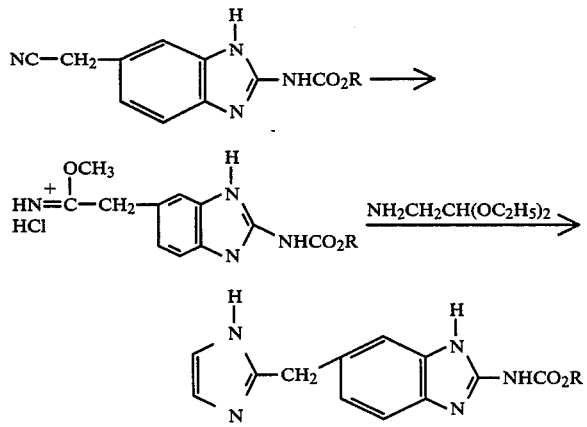

The method shown above is further exemplified by Example 3. To prepare compounds of the formula I wherein one of Y and Z is a group of the formula V, substitute 2-aminothiophenol for 2-aminoacetaldehydediethylacetal.

The following Examples further illustrate the preparation of the compounds of the present invention.

PREPARATION A

2-Nitro-5-(6-ethoxybenzothiazol-2-ylthio)aniline (Compound A)

To a stirred solution of 0.15 moles of potassium hydroxide in a mixture of 15 ml of water and 300 ml of dimethylformamide add 0.15 moles of 6-ethoxybenzothiazole-2-thiol (L. B. Sebrell and C. E. Boord, J. Am. Chem. Soc., 45, 2390 (1923)) under a nitrogen atmosphere. After complete dissolution, add 2-nitro-5-chloroaniline (R. C. Fuson, R. A. Dauman, E. Howard, Jr., and E. N. Marvell, J. Org. Chem., 12, 084 (1947)) and heat the mixture under reflux and a positive nitrogen pressure for about 16 hours. Pour the mixture into 1000 ml of water and remove the resulting precipitate. Wash the precipitate with water and crystallize from acetonitrile to give the title compound having a melting point of 126°–129° C.

EXAMPLE 1

Methyl 5(6)-[2-(6-ethoxybenzothiazolylthio)]benzimidazole-2-carbamate

Add 0.02 moles of Compound A to a slurry of 0.7 g of 5 percent ruthenium on carbon in 800 ml of absolute ethanol at 65° C. Then add 2 ml of hydrazine hydrate dropwise and heat the mixture under reflux for 1 hour. Add an additional 2 ml of hydrazine hydrate and continue heating for an additional 2½ hours. Remove the catalyst by filtration and replace the solvent with 125 ml of methanol. To this solution, add 0.022 moles of N-carbomethoxydimethyliminothiocarbonate (P. R. Atkins, S. E. Glue and T. Kay, J. Chem. Soc., Perkin I, 2645 (1973)) and 5 drops acetic acid. Heat the mixture under reflux for 20 hours to yield a solid precipitate which is removed by filtration. The melting point is 315° C. (dec.).

Similarly, selecting an appropriate compound of the formula Z—SH or Y—SH, wherein Y and Z are groups of the formula III, IV, VI, VII, VIII, XI or XII, prepare compounds of the formula I wherein one of Y and Z is hydrogen, $C_1$ to $C_4$ alkyl or $C_1$ to $C_4$ alkoxy. Examples of such compounds that may similarly be prepared are methyl 5(6)-[2-pyrimidylthio]benzimidazole-2-carbamate, methyl 5(6)-[2-benzimidazalylthio]benzimidazole-2-carbamate, methyl 5(6)-[2-benzothiazolylthio]benzimidazole-2-carbamate, and methyl 5(6)-(4-pyridylmethyl)benzimidazole-2-carbamate.

EXAMPLE 2

Methyl 5(6)-[6-(2,3-dihydrothiazolo[1,2-b]imidazolyl)]benzimidazole-2-carbamate

Add 10 g of N-acetylacetanilide, in small portions, to a stirred solution of 20 ml of 90% nitric acid and 40 ml of acetic anhydride at a temperature of −8° to −3° C. After 1 hour, dilute the reaction mixture with 300 g of ice water. The resulting solid, 4-acetyl-2-nitroacetanilide (Compound B), is filtered, washed and dried. The melting point is 133°–134° C.

Dissolve 10.8 g of Compound B in 30 ml of chloroform and treat the solution with 2.65 g of bromine in 20 ml of chloroform. Twenty minutes after decoloration, add 500 ml of diethyl ether and chill the mixture to give 10.4 grams of a light yellow solid (Compound C) having a melting point of 106°–106° C.

Dissolve 13 g of Compound C in 160 ml of acetone. Add 4.5 g of 2-aminothiazoline and stir at room temperature for one hour. Filter the resulting solid, 2-nitro-4-[alpha-(2-iminothiazolin-3-yl)acetyl]acetonilide hydrobromide (Compound D) wash it with acetone and then dry it. The melting point is 291°–292° C. (dec.).

Suspend 14 g, of Compound D in 100 ml of 10% ethanolic HCl and heat overnight. Filter the resulting suspension wash the solid, 2,3-dihydro-6-[3-nitro-4-aminophenyl]-imidazo-[1,2-b]thiazole hydrobromide (Compound E), with ethanol and then air dry it.

Suspend 5 g of Compound E and 1 g of 5% palladium on carbon in 150 ml of ethanol and hydrogenate at 60 psi until hydrogen absorption ceases. Filter the hydrogenated mixture, add 2.8 g of N-carbomethoxy-dimethyliminothiocarbonate in 100 ml of 90% ethanol to the filtrate and heat the mixture at reflux overnight. Remove the resulting solid, the title compound by filtration and air dry it. The melting point is 220° C. (dec.).

Substituting an appropriate compound of the formula

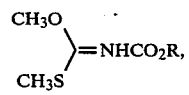

wherein R is ethyl, propyl or butyl, for the aforesaid N-carbomethoxy-dimethyliminothiocarbamate, similarly prepare alkyl analogues of the title compound.

EXAMPLE 3

(A) Methyl 5(6)-[2-imidazolylmethyl]benzimidazole-2-carbamate

In a flask containing 100 ml of a 1:1 mixture of 70% nitric acid and 98% sulfuric acid at a temperature of −5° to +5° C., place 29.3 g of 4-cyanomethylacetanilide and stir for one hour. Pour the mixture over 500 g of ice water and remove the resulting precipitate by filtration. Wash with distilled water and air dry to obtain 2-nitro-4-cyanomethylacetanilide (Compound F).

Hydrolyze 23.1 g of Compound F by refluxing in ethanolic HCl and then hydrogenate the product over 2 g of 5% palladium on carbon at an initial hydrogen gas pressure of 60 psi. Remove the catalyst by filtration and remove the solvent by evaporation. Dissolve the residue in a mixture of 150 ml ethanol, 150 ml distilled water and 5 ml acetic acid. To this solution add 11.7 g of N-carbomethoxydimethylthio-iminocarbonate and heat at reflux for 16 hours under a nitrogen atmosphere.

Separate the resulting precipitate from the reaction mixture and recrystallize from ethanol to obtain methyl-5(6)-cyanomethylbenzimidazole-2-carbamate (Compound G).

Suspend 4 g of Compound G in 100 ml of diethyl ether containing 3.65 g of HCl. Stir at 0° to 5° C. for 16 hours. Then, add 10 ml of dry methanol and stir for 2 additional hours. Replace the solvent by toluene and add 2.3 g of 2-aminoacetaldehydediethylacetal and stir for 4 additional hours while maintaining the mixture at 110° to 110° C. Remove the solvent by evaporation to obtain the title compound.

(B) Methyl 5(6)-[2-benzothiazolylmethyl]-benzimidazole-2-carbamate

Following the procedure of Example 3A, but substituting 2-aminothiophenol for 2-aminoacetaldehydediethylacetal, prepare the title compound.

The compounds of the present invention are useful in combatting helminths, i.e. in treating humans and animals suffering from an infestation of parasitic worms, for example, roundworms, hookworms, whipworms or tapeworms, by administering to the host animal a therapeutic amount of a compound of the present invention.

The compounds of this invention exhibit significant anthelmintic effects when administered to a host (e.g. mice, swine, dogs or ruminants) at doses as low as about one milligram of body weight per day in dosing over several days, or at about fifty milligrams per kilogram in a single day dosing, according to techniques well known in the art.

The optimum dose for each species of animal and for each type of parasite can readily be determined by one skilled in the art using standard techniques such as the Modified McMaster Egg Counting Technique as described by H. B. Whitlock and H. McL. Gordon, J. Council Scientific Industrial Research (Australia) 12, p. 50, 1939 and H. B. Whitlock, J. Council Scientific Research (Australia) 21, p. 177, 1948.

From these (and similar tests) anthelmintic efficacy is assessed by determining the number of eggs in feces passed on the days following treatment with the compound compared with pretreatment days. In addition, autopsy of animals after treatment will indicate whether the infection has been eradicated. Based on experimentation, proper dosages for curing various infections can be determined.

The compounds of this invention may be administered in suspensions, capsules, feed additive preparations, tablets, etc. as is well known to those skilled in the human and veterinary medical arts. In addition, the compounds may also be used as injectible anthelmintic preparations. For this purpose, the active ingredients, which should be sterile, may be admixed with suitable sterile carriers such as sterile water and isotonic saline solution to form solutions or suspensions.

Suitable clinical formulations containing the compounds of this invention can be administered orally in the form of tablets, capsules and the like.

Particularly useful anthelmintic formulations embodying the compounds of this invention for treatment of helminthiasis can be either as a liquid suspension ready to use or as a wettable or water-dispersible powder which is mixed with water prior to use.

A liquid-suspension formulation may contain from 50 to 55% w./v. (grams/liters) of the active compound (e.g. the title compound of Example 2, 3A or 3B) together with a dispersing agent and stabilizing agent. A typical formulation is as follows:

| | |
|---|---|
| Methyl 5(6)-[2-(6-ethoxybenzothiazoyl-thio)]benzimidazole-2-carbamate | 50 to 55 parts by weight |
| Dispersing agent | ½ to 2 parts by weight |
| Stabilizing agent | 1 to 3 parts by weight |
| Preservative | as required |
| Water | Sufficient to make 100 volumes. |

Suitable dispersing agents are those containing sulphonate groups, for example sodium lignin sulphonate or the sulphonated phenol or naphthol formaldehyde polymers. Bentonite may be employed as the stabilizing agent, although it is possible to use such protective colloids such as carboxy methyl cellulose, sodium alginate and the like. The formulations can be prepared by mixing the active compound and water containing dissolved dispersing agents very vigorously by means of suitable mechanical mixing equipment.

A wettable or water-dispersible powder formulation may contain about 90 to 95% w./w. of the active compound together with a wetting agent and dispersing agent. A diluent such a kaolin can also be added if a concentration below about 98% w./w. is required. An anti-forming agent, and, in some cases, a stabilizing agent may be present. A typical formulation is as follows:

| | |
|---|---|
| Methyl 5(6)-[2-(6-ethoxybenzothiazolyl-thio)]benzimidazole-2-carbamate | 90 to 95 parts by weight |
| Wetting agent | ¼ to 4 parts by weight |
| Stabilizing agent | 0 to 2 parts by weight |
| Anti-foaming agent | 0.01 to 1 parts by weight |
| Water | 0 to 5 parts by weight |

Suitable wetting agents are the non-ionic alkylphenolethylene oxide adducts, such as octylphenol or nonylphenol condensed with ten moles of ethylene oxide, or anionic materials such as the synthetic aryl alkyl sulphonates, or sodium dibutyl napthalene sulphonate. In general, about 1% w./w. wetting agent is required. The anti-foaming agent employed may be either silicone or such materials as ethyl hexanol, octanol and the like; and the stabilizing agent may again be chosen from bentonite or the water-soluble gums. Wettable or waterdispersible powder formulations are prepared by careful and adequate mixing of the active compound with other ingredients with or without the addition of some water using typical powder blending equipment such as a ribbon blender. The powder is stirred into water by the user before application in the field.

The following examples show particularly useful formulations:

| A. Tablet formulation | Grams per 1000 tablets |
|---|---|
| Methyl 5(6)-[2-(6-ethoxybenzothiazolyl-thio)]benzimidazole-2-carbamate | 200.0 |
| Lactose | 90.0 |
| Dicalcium phosphate, hydrous | 122.5 |
| Polyvinylpyrolidone | 25.0 |
| Polyethylenglycol 1500 | 7.5 |
| Corn Starch | 50.0 |
| Magnesium Stearate | 5.0 |
| | 500.0 |

Mix the active compound, the lactose and the dicalcium phosphate. Dissolve the polyethyleneglycol 1500 and the polyvinylpyrolidone in approximately 20 ml of water. Granulate the powder blend with the water solution, adding additional water if necessary, to produce a damp mass. Pass the wet granulation through a 12 mesh screen; spread on trays and air dry at 35° C. Blend the dry granulates with the starch and the magnesium stearate. Compress into 500 mg tablets.

| B. Capsule formulation | Grams per 1000 capsules |
|---|---|
| Methyl 5(6)-[2-(6-ethoxybenzothiazolyl-thio)]benzimidazole-2-carbamate | 200.0 |
| Lactose | 198.0 |
| Magnesium Stearate | 2.0 |
| | 400.0 |

Blend the ingredients and fill into hard gelatine capsules.

| C. Injectable formulation | mg/ml |
|---|---|
| Methyl 5(6)-[2-(6-ethoxybenzothiazolylthio)]benzimidazole-2-carbamate | 25.0 |
| Dimethyl Acetamide | 200.0 |
| Benzyl Alcohol | 20.0 |
| Polyethylene glycol 400 to q.s. | 1.0 ml |

Combine the above ingredients using standard techniques.

| D. Injectable formulation | mg/ml |
|---|---|
| Methyl 5(6)-[2-(6-ethoxybenzothiazolylthio)]benzimidazole-2-carbamate | 25.0 |
| Dimethyl Acetamide | 200.0 |
| Benzyl Alcohol | 20.0 |
| Propylene Glycol to q.s. | 1.0 ml |

Combine the above ingredients using standard techniques.

| E. Injectable formulation | mg/ml |
|---|---|
| Methyl 5(6)-[2-(6-ethoxybenzothiazolylthio)]benzimidazole-2-carbamate | 50.0 |
| Dimethyl Acetamide | 300.0 |
| Benzyl Alcohol | 20.0 |
| Polyethylene glycol 400 to q.s. | 1.0 ml |

Combine the above ingredients using standard techniques.

Similarly, prepare formulations using other compounds of the present invention, e.g. methyl 5(6)-[6-(2,3-dihydrothiazolo 1,2-b imidazolyl)]benzimidazole-2-carbamate; methyl 5(6)-[2-imidazolylmethyl]benzimidazole-2-carbamate; and methyl 5(6)-[2-benzothiazolylmethyl]-benzimidazole-2carbamate.

I claim:

1. A compound of the formula

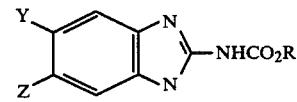

wherein R is alkyl having 1 to 4 carbon atoms; one of Y and Z is a heterocyclic moiety selected from groups of the formula

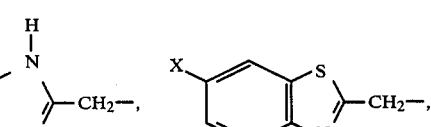

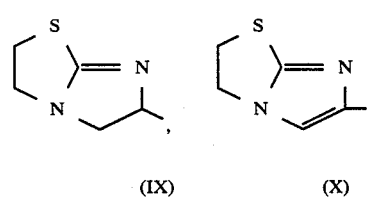

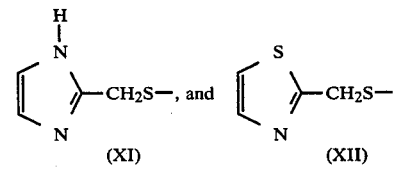

wherein X is alkyl having 1 to 4 carbon atoms, alkoxy having 1 to 4 carbon atoms or hydrogen, and the other of Y and Z is hydrogen, alkyl having 1 to 4 carbon atoms or alkoxy having 1 to 4 carbon atoms.

2. A compound according to claim 1, wherein R is methyl, Y is hydrogen and Z is a group of the formula X.

3. A compound according to claim 1 wherein R is methyl, Y is hydrogen, and Z is a group of the formula II.

4. A compound according to claim 1 wherein R is methyl, Y is hydrogen, and Z is a group of the formula V.

5. A method of treating helminth infestation in mammals which comprises administering to an infected mammal an effective amount of a compound as claimed in any one of claims 2, 1 3 or 4.

6. A pharmaceutical composition, useful as an anthelmintic, comprising an effective amount of a compound as claimed in any one of claims 2, 1, 3 or 4 together with a pharmaceutically acceptable carrier.

7. An animal feed or drink, having anthelmintic properties, comprising a feed mix or liquid carrier and an effective amount of a compound as claimed in any of claims 2, 1, 3 or 4.

8. An injectable pharmaceutical composition, useful as an anthelmintic, comprising an effective amount of a compound as claimed in any one of claims 2, 1, 3 or 4 together with a pharmaceutically acceptable carrier.

* * * * *